(12) United States Patent
Oberkamp et al.

(10) Patent No.: US 6,485,499 B1
(45) Date of Patent: Nov. 26, 2002

(54) HARD DRIVE VITRECTOMY CUTTER

(75) Inventors: Dennis L. Oberkamp, Grover Beach, CA (US); Billie John Barwick, Jr., San Luis Obispo, CA (US)

(73) Assignee: Advanced Medical Optics, Santa Ana, CA (US)

( * ) Notice: Subject to any disclaimer, the term of this patent is extended or adjusted under 35 U.S.C. 154(b) by 0 days.

(21) Appl. No.: 09/257,885

(22) Filed: Feb. 25, 1999

(51) Int. Cl.⁷ .............................................. A61B 17/32
(52) U.S. Cl. ..................................................... 606/171
(58) Field of Search .............................. 606/166, 170, 606/180, 171, 184, 185, 169, 159; 604/22

(56) References Cited

U.S. PATENT DOCUMENTS

| | | | |
|---|---|---|---|
| 3,815,604 A | * 6/1974 | O'Malley et al. | 604/22 |
| 4,203,444 A | * 5/1980 | Bonnell et al. | 604/22 |
| 4,598,710 A | 7/1986 | Kleinberg et al. | |
| 4,696,298 A | 9/1987 | Higgins et al. | |
| 4,819,635 A | 4/1989 | Shapiro | |
| 4,850,354 A | 7/1989 | McGurk-Burleson | |
| 4,909,249 A | 3/1990 | Akkas et al. | |
| 5,106,364 A | 4/1992 | Hayafuji et al. | |
| 5,176,628 A | 1/1993 | Charles et al. | |
| 5,284,472 A | 2/1994 | Sussman et al. | |

* cited by examiner

Primary Examiner—Kevin T. Truong
(74) Attorney, Agent, or Firm—Walter A. Hackler; Peter Jon Gluck

(57) ABSTRACT

A hard drive vitrectomy cutter generally includes a hand held probe for cutting tissue of a body, and a mechanical system for driving cutting action of the probe. The probe includes an outer sleeve having a perforation therein for receiving a portion of tissue, and a cutter sleeve, coaxially disposed within the cutter sleeve, for shearing the portion from the body of tissue. Importantly, the mechanical system for driving the probe includes a coaxial cable having a stationary outer cable and a slidable inner cable, said coaxial cable being connected with a stepper motor adapted for moving the inner cable axially within the outer cable. The inner cable is mounted in operative relationship with the cutter sleeve such that the stepper motor may be operated to move the inner cable and consequently drive cutting strokes of the cutter sleeve. A spring may be included for biasing the cutter sleeve against a pulling force exerted by the stepper motor. An aspiration line may also be included for pulling the portion of tissue into the perforation and subsequently removing the sheared portion from the probe.

13 Claims, 1 Drawing Sheet

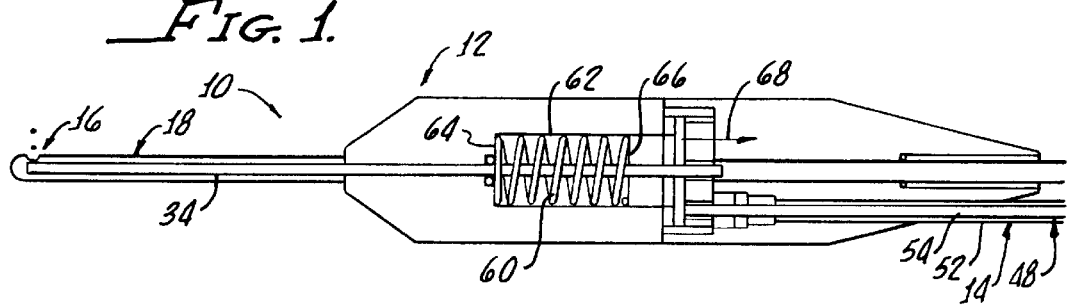
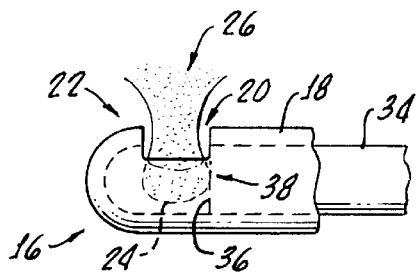
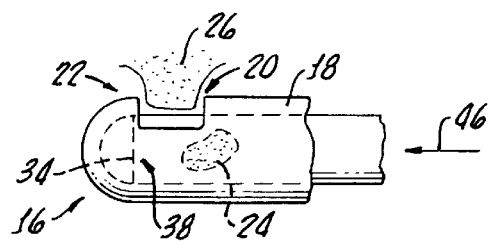
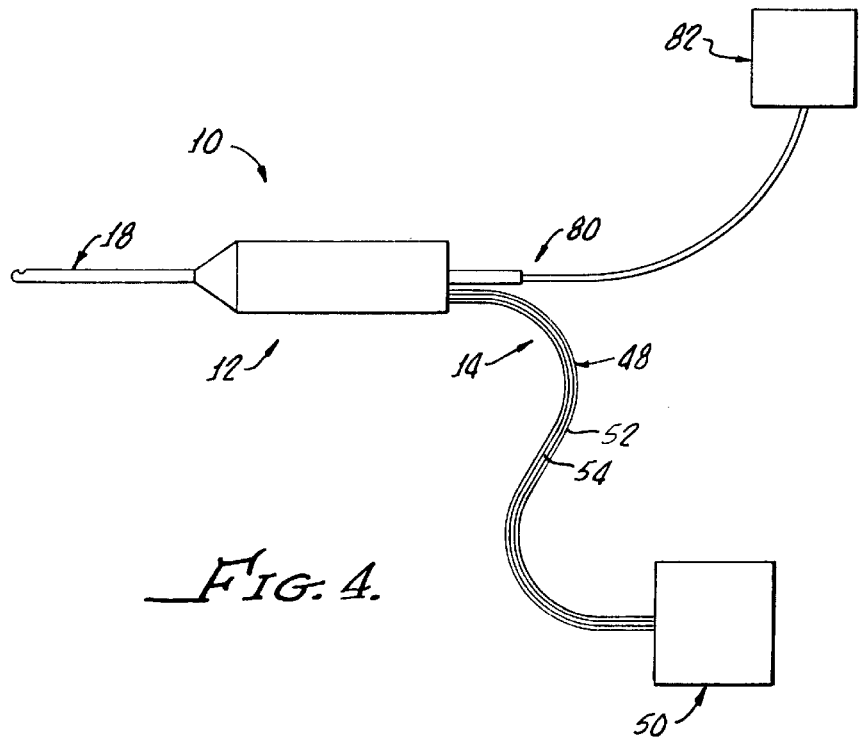

HARD DRIVE VITRECTOMY CUTTER

The present invention generally relates to surgical instruments and more particularly relates to a tissue cutting surgical device suitable for use in vitreous and retinal surgery.

An eye surgery procedure performed behind the lens is called vitreous surgery in as much as the posterior chamber of the eye is filled with a transparent jelly called the vitreous humor ("vitreous").

Understandably, vitreous surgery, as with any ophthalmic surgical procedure, requires great precision. The vitreous is filled with numerous fiber like materials, some of which are attached to the delicate retina. The presence of these fibers make vitreous surgery quite difficult, due to the possibility of retinal injury occurring if one of these fibers is inadvertently severed.

Moreover, retinal surgery, which involves actual cutting of the retina of the eye, must be performed with even greater precision, as the retina is the immediate instrument of vision and is directly connected with the brain by the optic nerve. Thus, a surgical instrument suitable for use in vitreous surgery may not be suitable for use in retinal surgery.

For example, the state of the art vitreous cutter comprises a hand held probe having a cutting tip thereon.

The cutting tip comprises an outer tube having a perforation therein, and an inner tube having a reciprocating cutting edge for shearing portions of tissue drawn into the outer tube perforation. The inner tube is typically driven in an axially reciprocating fashion, at a cutting rate of about 400 strokes per minute, by pneumatic means. More particularly, the pneumatic means typically includes a pressurized air source which supplies periodic bursts of air that drive the inner tube forward within the outer tube. A diaphragm or spring is included in the probe which biases the inner cutting tube backward to a home position. Thus, the cutting strokes of the inner tube are controlled by periodic bursts of air forcing the inner cutting tube forward, alternating with the discontinuing thereof such that the biased spring forces the cutting tube backward.

It well known that such pneumatically driven devices do not operate effectively at very low speeds and are designed for operation at high speeds, for example, hundreds of cycles per minute. Moreover, although the cutting rate provided by such instruments may be controllable to some extent, control over speed and length of an individual cutting stroke is not obtainable. Thus, such cutters may be inappropriate for use in retinal surgery, which requires exceptional precision and control in order to avoid serious injury to the patient.

The present invention provides a ophthalmic surgical cutting instrument that can be operated at very low speeds in order to provide to superior control of cuts made thereby. The instrument in accordance with the present invention may also be operated quite effectively at high speeds when the nature of the surgery so requires.

SUMMARY OF THE INVENTION

Accordingly, a surgical cutting device in accordance with the present invention generally comprises a probe having a cutting tip comprised of an outer sleeve and an inner cutter sleeve. This type of cutting tip, as will now be generally described, is presently well known in the art. More specifically, the outer sleeve includes a perforation proximate a distal end of the outer sleeve which provides means for receiving a portion of tissue to be incised. The cutter sleeve is slidably and coaxially disposed in the outer sleeve and includes a cutting edge at a distal end thereof. When the probe tip is urged against a portion of tissue, such as a portion of the vitreous humor, the portion will protrude through the perforation in the outer sleeve and be sheared by a axially reciprocating motion of the cutter sleeve.

Importantly, the present invention also comprises mechanical means for driving the stroking motion of the cutter sleeve at a selected stroke rate of down to about one stroke per minute, or in other words, at an exceptionally slow speed. The mechanical means, which will be described in greater detail hereinafter, enable a physician to control amount and speed of individual strokes of the stroking motion. Moreover, the present invention enables a physician to achieve even a fraction of a cut, if so desired.

More particularly, the mechanical means includes a coaxial cable as means for connecting the probe to a motor adapted for moving the cutter sleeve in an incremental or stroking motion, for example a stepper motor. The cable may comprise an outer stationary cable and an inner cable slidably disposed therein and mounted in operative relationship with the cutter sleeve. A spring may be included within the probe for biasing the cutter sleeve in a home position. Thus, the inner cable and reciprocating cutter sleeve are moved back and forth by alternating forces exerted by the stepper motor and the spring.

An aspiration line, in fluid communication with a bore in the cutter sleeve, may also be provided. More particularly, the aspiration line may be connected to a vacuum source, and may provide means for both gently drawing the portion of tissue into the outer tube perforation and subsequently removing the portion of tissue from the probe to a collection vessel after the cutter sleeve has severed said portion as described hereinabove.

By selection of an appropriate stepper motor, the cutter sleeve may be driven at a selected stroking rate of between about one and about one thousand or more cuts per minute.

BRIEF DESCRIPTION OF THE DRAWINGS

The advantages and features of the present invention will be better understood by the following detailed description when considered in conjunction with the accompanying drawings in which:

FIG. 1 shows a cross sectional view of an embodiment of the present invention including a probe for cutting tissue of a body, said probe including a tip having an outer sleeve and an inner cutter sleeve, and mechanical means for driving the cutter sleeve at a stroking rate of down to about one stroke per minute;

FIG. 2 shows the probe tip of the embodiment shown in FIG. 1 as a portion of tissue to be cut is being drawn into the tip through a perforation in the outer sleeve;

FIG. 3 shows the portion of tissue after it has been sheared by a stroking motion of the cutter sleeve; and FIG. 4 shows a schematic diagram of an embodiment of the present invention including a stepper motor for driving the mechanical means.

DETAILED DESCRIPTION

Turning now to FIG. 1, there is shown a surgical cutting device 10, in accordance with the present invention, which generally includes a probe 12 as means for cutting tissue of a body (not shown in FIG. 1), and mechanical means 14 for driving the cutting action of the probe 12.

More particularly, the probe 12 includes a tip 16 thereon which is shown in detail in FIGS. 2 and 3. The tip 16 includes an outer sleeve 18 having an opening, or perforation 20, proximate a distal end 22 of the outer sleeve 18 as means for receiving a portion 24 of tissue to be cut from the body 26 of tissue. The body 26 of tissue may be a vitreous humor of an eye, a retina of the eye, or any other body of tissue located in a confined area of a patient, such as to require the use of a narrow probe to access same.

The tip 16 also includes a cutter sleeve 34, coaxially disposed within the outer sleeve 18, for shearing the portion 24 of tissue by a stroking motion thereof with respect to the outer sleeve 18. The cutter sleeve 34 includes a cutting edge 36 on a distal end 38 thereof which severs the portion 24 of tissue received through the perforation 20 as the cutter sleeve 34 is moved in the direction of arrow 46.

Although a simple coaxial sleeve cutting tip 16 is hereinabove described and shown in the drawings, any other suitable probe tip of the shearing or scissor type, as are currently known in the art, may be used with the present invention. Materials construction for the probe 12 and probe tip 16 may be of plastic or metal of combinations thereof, all suitable for use in surgical applications.

Importantly, the mechanical means 14 in accordance with the present invention provides a means for enabling a surgeon to use the probe 12 with maximum control over speed and length of tissue cuts. In other words, the stroking motion of the cutter sleeve 34 may be driven at a selected stroke rate from as slow as one or two strokes per minute, up to as fast as about a thousand strokes per minute, depending upon the particular surgical application. For example, for delicate retinal surgery, the cutter sleeve 34 may be driven at a very slow stroking rate, such that the physician has maximum control over each individual cut and can perform fractions of cuts if desired. On the other hand, for vitreous surgery where some or all of the vitreous is to be removed from the eye, a higher stroking rate may be preferable. Of course, a physician may alternate between high and low speeds in a single surgical procedure if desirable.

Now, referring to both FIGS. 1 and 4, the mechanical means 14 may include a cable 48 which provides means for connecting the probe 12 to a stepper motor 50 adapted to move the cutter sleeve 34 in the stroking motion. More particularly, the cable 48 may be a flexible coaxial cable comprised of an outer stationary cable 52 and an inner cable 54 slidably disposed therein.

The inner cable 54 is preferably mounted in operative relationship with the cutter sleeve 34 such that an axial motion along a length of the inner cable 54 within the stationary outer cable 52 causes a complementary motion of the cutter sleeve 34. The cable 48 is connected to the stepper motor 50 in a conventional fashion such as to cause incremental sliding motions of the inner cable 54 in a highly controlled manner. Preferably, the stepper motor 50 is connected to the cable 48 such that the motor 50 drives the inner cable 54 in an incremental, pull and release fashion.

As shown in FIG. 1, the probe 12 may include a spring 60 therein as a means for biasing the cutter sleeve 34 against a pulling force applied thereto by the inner cable 54 and motor 50. For example, the spring 60 may be disposed in a chamber 62, and may be connected to a fixed wall 64 and a slidable wall 66 defining boundaries of the chamber 62.

More particularly, the cutter sleeve 34 and the inner cable 54 may be mounted in a conventional fashion to the slidable wall 66 such that the spring 60 biases the cutter sleeve 34 toward the distal end 22 of the outer sleeve 18, as shown in FIG. 3.

In operation, upon each controlled pull of the inner cable 54 by the motor 50, the slidable chamber wall 66 is forced in the direction of arrow 68, thus elongating, or stretching the spring 60 and moving the cutter sleeve 34 away from the distal end 22 to a right most position, such as shown in FIG. 2. The portion 24 of tissue is thus able to enter the perforation 20 within the outer sleeve 18, which may be aided by use of suction (as will be described in more detail hereinafter). Subsequently, upon each controlled release, or discontinuing of pulling by the motor 50, the stretched spring 60 pulls the cutter sleeve 34 back toward the distal end 22, or home position, consequently cutting the portion 24 from the body 26 of tissue (FIG. 3). Repetitions of this operation enable cutting of a desire d a mount of tissue.

Importantly, a gradual and steady release of pulling on the inner cable 54 by the stepper motor 50 in cooperation with a spring 60 operates to prevent uncontrollable rebounding motions of the cutter sleeve 34 when the device 10 is operated at slow speeds.

By adjustment of conventional controls (not shown) on the stepper motor 50, a physician is able to shear tissue at a stroke rate ranging from exceptionally slow speeds to very high speeds. When operated at a low speed, for example, one or two deliberate strokes per minute, the device 10 enables a physician to perform precise cuts or fractions of cuts with precision.

Referring now to FIGS. 1 through 4, preferably, the present invention includes an aspiration line 80 which provides means for both gently drawing the portion 24 of tissue into the outer sleeve perforation 20 and subsequently removing the portion 24 from the probe 12 after it has been sheared. This may be accomplished in any suitable conventional manner such as by providing a vacuum source 82 as shown in FIG. 4.

Although there has been hereinabove described a hard drive vitrectomy cutter, in accordance with the present invention, for the purpose of illustrating the manner in which the invention may be used to advantage, it will be appreciated that the invention is not limited thereto. Accordingly, any and all modifications, variations, or equivalent arrangements which may occur to those skilled in the art should be considered to be within the scope of the invention as defined in the appended claims.

What is claimed is:

1. A surgical cutting device comprising:
   probe means for cutting tissue of a body, said probe means comprising
      an outer sleeve including perforation means, proximate a distal end of said out sleeve, for receiving a portion of the tissue, and
      cutter sleeve means, coaxially disposed within the outer sleeve, for shearing the portion of tissue by a linear motion thereof with respect to the outer sleeve; and
   non-pneumatic mechanical means for driving of the stroking motion of the cutter sleeve means at a selected stroke rate of less than two strokes per minute.

2. The surgical cutting device according to claim 1 wherein the mechanical means includes cable means for connecting the probe means to a stepper motor adapted to move the cutter sleeve means in the stroking motion.

3. The surgical cutting device according to claim 2 wherein the cable means includes an outer stationary cable and an inner cable slidably disposed therein, said inner cable being mounted in operative relationship with the cutter sleeve means.

4. The surgical cutting device according to claim 3 wherein the mechanical means further includes spring means for biasing the cutter sleeve means against a pulling force applied thereto by the stepper motor.

5. The surgical cutting device according to claim 2 further comprising a stepper motor connected to the cable means.

6. The surgical cutting device according to claim 1 further comprising aspiration means for drawing the portion of tissue into the outer sleeve perforation and for removing the portion of tissue from the probe means.

7. A surgical cutting device comprising:

probe means for cutting tissue of a body, said probe means comprising
- an outer sleeve including perforation means, proximate a distal end of said outer sleeve, for receiving a portion of the tissue, and
- non-pneumatic cutter sleeve means, coaxially disposed within the outer sleeve, for shearing the portion of tissue by a linear motion thereof with respect to the outer sleeve; and mechanical means for driving of the linear motion of the cutter sleeve means at a selected stroke rate of between about one and about 1000 strokes per minute.

8. An ophthalmic surgical cutting device comprising:

probe means for cutting tissue of an eye, said probe means including
- an outer sleeve including perforation means for receiving a portion of the tissue, and
- cutter sleeve means, coaxially disposed within said outer sleeve, for shearing the portion by a linear motion of the cutter sleeve with respect to the outer sleeve; and non-pneumatic mechanical means for enabling control of individual strokes of the linear motion, said mechanical means including cable means for connecting the probe means to a stepper motor in order to drive the linear motion of the cutter sleeve means.

9. The ophthalmic surgical cutting device according to claim 8 wherein said cable means includes an outer stationary cable and an inner cable slidably disposed therein, said inner cable being mounted in operative relationship with the cutting sleeve means.

10. The ophthalmic surgical cutting device according to claim 9 wherein the mechanical means further includes spring means for biasing the cutter sleeve means against a pulling force applied thereto by the stepper motor.

11. The ophthalmic surgical cutting device according to claim 10 further comprising aspiration means for drawing the portion of tissue into the outer sleeve perforation and for removing the portion of tissue from the probe means.

12. The ophthalmic surgical cutting device according to claim 8 further comprising a stepper motor connected to the cable means.

13. An ophthalmic surgical cutting device comprising:

probe means for cutting tissue of an eye, said probe means including
- an outer sleeve including perforation means for receiving a portion of the tissue, and
- cutter sleeve means, coaxially disposed within said outer sleeve, for shearing the portion by a linear motion of the cutter sleeve with respect to the outer sleeve; and mechanical means for enabling control of individual strokes of the linear motion, said mechanical means including
- an outer stationary cable and an inner cable slidably disposed therein, said inner cable being mounted in operative relationship with the cutter sleeve means,
- stepper motor means, connected to the inner cable, for driving the linear motion of the cutter sleeve means, and
- spring means for biasing the cutter sleeve means against a pulling force applied thereto by the stepper motor; and aspiration means for drawing the portion of tissue into the outer sleeve perforation and for removing the portion of tissue from the probe means.

* * * * *